(12) United States Patent
Sanandajifar (10) Patent No.: US 11,222,108 B2
(45) Date of Patent: Jan. 11, 2022

(54) CONNECTOR-BASED OPTICAL POWER MODULATED IDENTIFICATION APPARATUS AND METHOD

(71) Applicant: KARL STORZ Imaging, Inc., Goleta, CA (US)

(72) Inventor: Joseph Sanandajifar, West Hills, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 303 days.

(21) Appl. No.: 16/409,106

(22) Filed: May 10, 2019

(65) Prior Publication Data

US 2019/0272369 A1    Sep. 5, 2019

Related U.S. Application Data

(63) Continuation of application No. 15/614,483, filed on Jun. 5, 2017, now Pat. No. 10,331,877.

(51) Int. Cl.
*G06F 21/00* (2013.01)
*G06F 21/44* (2013.01)
*A61B 1/00* (2006.01)
*A61B 90/90* (2016.01)

(52) U.S. Cl.
CPC .......... *G06F 21/44* (2013.01); *A61B 1/00013* (2013.01); *A61B 1/00059* (2013.01); *A61B 90/90* (2016.02)

(58) Field of Classification Search
CPC . A61B 1/00059; A61B 90/90; A61B 1/00013; G06F 21/44
See application file for complete search history.

(56) References Cited

U.S. PATENT DOCUMENTS

| | | | |
|---|---|---|---|
| 4,878,896 A | 11/1989 | Garrison | |
| 6,685,701 B2 | 2/2004 | Orszulak | |
| 8,419,622 B2 | 4/2013 | Shimotsu | |
| 8,556,521 B2 | 10/2013 | Everett | |
| 9,195,008 B2 | 11/2015 | Farnan | |
| 2004/0042063 A1* | 3/2004 | Ohtani | H04B 10/2937 359/341.3 |
| 2004/0113498 A1 | 6/2004 | Kroenke | |
| 2004/0122419 A1 | 6/2004 | Neuberger | |
| 2004/0243120 A1* | 12/2004 | Orszulak | A61B 18/14 606/34 |
| 2009/0096894 A1 | 4/2009 | Amling | |

(Continued)

*Primary Examiner* — Tri M Tran
(74) *Attorney, Agent, or Firm* — Michael J Loi; David Noel Villalpando (57) ABSTRACT

An apparatus includes a device interface system having a first connector and second connector, each with a respective optical signal path arrangement operatively aligned when the two connectors are in a connected position. The operative alignment allows a base optical signal to be transmitted from the first connector to the second connector. An optical signal modification arrangement is included in the second connector and is operable to provide a predefined modification to the base optical signal to result in an optical ID signal that is transmitted back to the first connector. An identification processing unit associated with the first connector receives an ID input signal corresponding to the optical ID signal and produces an identification output responsive to the ID input signal.

18 Claims, 8 Drawing Sheets

(56) References Cited

U.S. PATENT DOCUMENTS

2010/0027943 A1  2/2010  Armani
2011/0200327 A1  8/2011  Qi
2014/0243120 A1  8/2014  Chauvin

* cited by examiner

CONNECTOR-BASED OPTICAL POWER MODULATED IDENTIFICATION APPARATUS AND METHOD

CROSS-REFERENCE TO RELATED APPLICATION

This application is a continuation of U.S. application Ser. No. 15/614,483, filed Jun. 5, 2017, issued as U.S. Pat. No. 10,331,877 on Jun. 25, 2019, and entitled "Connector-based optical identification apparatus and method," that is hereby incorporated by reference.

TECHNICAL FIELD OF THE INVENTION

The invention relates to apparatus and methods which can be employed to identify a device when it is connected in a system. For example, the present identification apparatus may be employed to identify a medical instrument such as an endoscope as the instrument is connected to a control unit for the instrument.

BACKGROUND OF THE INVENTION

Many types of devices such as instruments for medical and other applications operate through a connection to a separate control unit which provides power and control signals, and may also receive data or some other output from the connected device. In some cases there is some degree of interchangeability in the types of devices that may be physically connected to a given control unit. In these cases it is necessary to ensure that the intended device is connected to the control unit for a given application of the system. However, it may be difficult for device operators to distinguish between different devices which may have similar appearance and differ only in technical capability. Also, particularly medical instruments may be limited to a maximum number of uses or a maximum number of uses before some manner of service is required to ensure proper operation of the instrument.

Systems have been developed to assist in identifying a device such as a medical instrument to be connected in a system for operation. For example, U.S. Patent Application Publication No. 2004/0122419 A1 discloses a system particularly for use in recognizing disposable or reusable optical components that may be connected to a radiation source unit, and for maintaining usage information on such optical components. The system disclosed in this publication employs a radio frequency identification (RFID) transponder located with the connectable device to communicate with the unit to which it is connected. However, radio frequency devices such as these are susceptible to electromagnetic interference which can limit the application and effectiveness of the system.

U.S. Pat. No. 4,878,896 to Garrison et al. discloses an identification arrangement for use with a medical infusion system. The system disclosed in this patent employs a series of light sources and light sensors located on an infusion pump. The light sources and light sensors cooperate with elements on a pump-mounted cassette to provide identification information regarding the cassette. The identification arrangement disclosed in Garrison et al. is cumbersome and not suited for use in many applications in which connected device identification is desired.

SUMMARY OF THE INVENTION

It is an object of the present invention to provide an identification apparatus that may be associated with an arrangement of connectors providing an interface between a device and a control unit for the device. The invention encompasses an apparatus including both connecter-mounted components and a processing unit which need not be mounted on a connector. The invention also encompasses an arrangement of connector-mounted components to facilitate device identification, an instrument having a connector incorporating identification components, and methods for providing an identification output after a connection between a device and a control unit for the device.

An apparatus according to one aspect of the present invention includes a device interface system having a first connector and second connector. The first connector includes an optical signal transmission path arrangement and an optical signal receiving path, while the second connector includes an optical signal return path arrangement extending from an input end to an output path. The second connector is configured to connect to the first connector in an operating position in which the input end of the optical signal return path arrangement is operatively aligned with the optical signal transmission path arrangement and the output path is operatively aligned with the optical signal receiving path. Operative alignment in this sense and as used elsewhere in this disclosure and the claims means that the optical signal paths are aligned so that optical energy may propagate from one optical path to the other with only acceptable losses under the circumstances. The apparatus according to this aspect of the present invention also includes an optical signal modification arrangement operable to provide a predefined modification to a base optical signal applied at the input end of the optical signal return path arrangement. This predefined modification results in an optical ID signal applied at the output path of the optical signal return path arrangement. An optical transmitter arrangement and an optical receiver are also included in the apparatus. The optical transmitter arrangement is operable to apply the base optical signal including two or more optical signal components to the optical signal transmission path arrangement, while the optical receiver is operable to receive the optical ID signal from the optical signal receiving path and produce an ID input signal responsive to the received optical ID signal. An identification processing unit which receives the ID input signal produces an identification output responsive to the ID input signal.

According to this first aspect of the present invention, the predefined modification which may be applied to the base optical signal when the first and second connectors are in the operating position encodes information about the second connector or a device associated with the second connector into the base optical signal and thereby produces the optical ID signal. This information may be correlated to one or more characteristics of the second connector or device associated with the second connector. For example, the second connector may comprise a connector of a medical instrument which is adapted to connect to a complementary connector of a control unit for the medical instrument. The optical ID signal, that is, the base optical signal modified according to the predefined modification, may correlate to a type of medical instrument, operating parameters or limitations of the medical instrument, or perhaps a specific identifier for the medical instrument such as a serial number for the instrument. Regardless of the characteristics of the second connector or the connected device which may be discerned by an analysis of the optical ID signal, the identification output may prompt any number of responses appropriate to the situation. In the medical instrument example, the identification output may prompt the medical instrument control unit to power up the connected medical instrument and/or send data such as operating parameters to the medical instrument. Alternatively, in the event the detected characteristic of the connected medical instrument indicates that the medical instrument is inappropriate in some fashion, the identification output may prevent the medical instrument control unit from powering up the instrument or otherwise cause the instrument to be inoperable.

An identification apparatus according to this first aspect of the invention allows characteristics of a device such as a medical instrument to be identified upon connection to a control unit prior to any power being applied to the instrument and without any electronic communications to or from the instrument. With the absence of electronic communications to or from the instrument, the identification process may be entirely immune to electromagnetic interference which could affect the accuracy of the identification. Embodiments according to this first aspect of the invention may also ensure that the required electrical isolation barrier is maintained across the connectors. Also, the identification apparatus is capable of providing large amounts of data for identification while maintaining a very compact form factor.

In an apparatus according to the first aspect of the invention, the identification processing unit may comprise data storage and a suitable processor. The data storage stores a number of ID signatures with each respective ID signature being related in the data storage arrangement to respective connectable device information, such as a device type, serial number, or other device-specific information. The processor is operable to, in response to the received ID input signal, locate a stored ID signature corresponding to the ID input signal and then retrieve the respective connectable device information related to the located ID signature. The processor then generates the identification output based on the retrieved device information.

In this disclosure and the following claims the term "arrangement" when used in connection with an optical signal path or other physical structure means that the referenced physical structure may include one or more components. For example, an optical signal path arrangement may include one or more optical paths such as optical waveguides for carrying the different optical components of an optical signal. Each respective optical component may be carried by a respective optical waveguide in the optical signal path arrangement. Thus an optical signal transmission path arrangement according to the first and other aspects of the present invention may include a number of different transmission optical waveguides corresponding to the number of optical components included in the base optical signal. Similarly, the optical signal return path arrangement may include a number of different return optical waveguides corresponding to the number of optical components included in the base optical signal. Implementations having multiple different return optical waveguides may include an optical coupler to optically couple each return optical waveguide to the output optical waveguide of the second connector.

An apparatus according to another aspect of the present invention includes an instrument such as a medical or industrial instrument and a connector to the instrument. The instrument connector may also be referred to as a device-side connector and is configured to connect in an operating position with a control unit connector, that is, a control unit-side connector, associated with a control unit for the instrument. An apparatus according to this second aspect of the present invention further includes an optical signal return path arrangement mounted in the instrument connector and also includes an optical signal modification arrangement associated with the optical signal return path arrangement. The optical signal return path arrangement here corresponds to the optical signal return path arrangement discussed above in connection with the previously described aspect of the invention. Similarly, the optical signal modification arrangement corresponds to that element of the previously described aspect of the invention.

In one implementation according to either of the foregoing aspects of the invention, the optical signal modification arrangement comprises at least one optical signal attenuator. Where the optical signal return path arrangement includes multiple return optical waveguides, each respective optical attenuator may be operatively connected in a respective one of the return optical waveguides. Otherwise, each optical attenuator may comprise a device that selectively attenuates a given base optical signal component propagating along a single waveguide. These alternatives will be described in further detail below in connection with a representative embodiment and variations on that embodiment.

In another implementation according to either of the foregoing aspects of the invention including two or more return optical waveguides, the return optical waveguides may each include a respective end portion extending substantially parallel to an output end of the output optical waveguide. Similarly, in implementations according to the first aspect of the present invention having two or more transmission optical waveguides, each such waveguide may include a respective transmission end portion extending substantially parallel to a receiving end portion of the receiving optical waveguide. This arrangement of optical waveguides facilitates a compact assembly of the connector-mounted components of the identification apparatus with the component aligned across an interface plane between the connectors in the operating position.

In another implementation according to either of the foregoing aspects of the invention, the optical signal return path arrangement is mounted in a return unit in the second connector. The return unit may include a return alignment block which is mounted in the second connector. Similarly, in an implementation according to the first aspect of the invention, the optical signal transmission path arrangement and the optical signal receiving path are mounted within a send/receive unit of the first connector which may include a send/receive alignment block.

Another aspect of the invention includes a method for identifying a connector or a device associated with a connector. The method according to this aspect of the invention includes transmitting the base optical signal from a first connector to a second connector, and directing the base optical signal along the optical return path arrangement associated with the second connector. The method further includes applying a predefined modification pattern to the two or more base optical signal components of the base optical signal as the signal is directed through the optical signal return path arrangement. As in the first aspect of the invention described above, this predefined modification pattern results in an optical ID signal applied at the output waveguide of the optical signal return path arrangement. The method also includes directing the optical ID signal from the output waveguide to a receiving optical waveguide of the first connector, receiving the optical ID signal at the first connector and producing an identification output in response to the received optical ID signal.

As in the previously described aspects of the present invention, the predefined modification pattern may be a pattern of signal attenuation among the two or more base optical signal components. Also, each base optical signal component may be transmitted or directed over a different optical waveguide in the respective optical signal path arrangement.

According to any of the above-described aspects of the invention, the two or more base optical signal components may be offset temporally. Furthermore, each of the two or more base optical signal components may be transmitted at a different respective modulation frequency or other characteristic which facilitates encoding information into the base optical signal itself.

These and other advantages and features of the invention will be apparent from the following description of representative embodiments, considered along with the accompanying drawings.

DESCRIPTION OF REPRESENTATIVE EMBODIMENTS

The various aspects of the present invention are described below in the context of an observation instrument system, particularly an endoscopic system. However, the present invention is not limited to this representative application. Thus, observation instruments (e.g., a video cameras, endoscopes, exoscopes, borescopes) employing high-resolution imaging (e.g., a 4K resolution design) represent merely an illustrative, but non-limiting example application of various aspects of the present invention. More generally, an apparatus and method within the scope of the following claims may have application in substantially any interface system to a given device in which it is desirable to automatically identify some characteristic of the given device at the time it is connected via the interface system.

Figure 1:
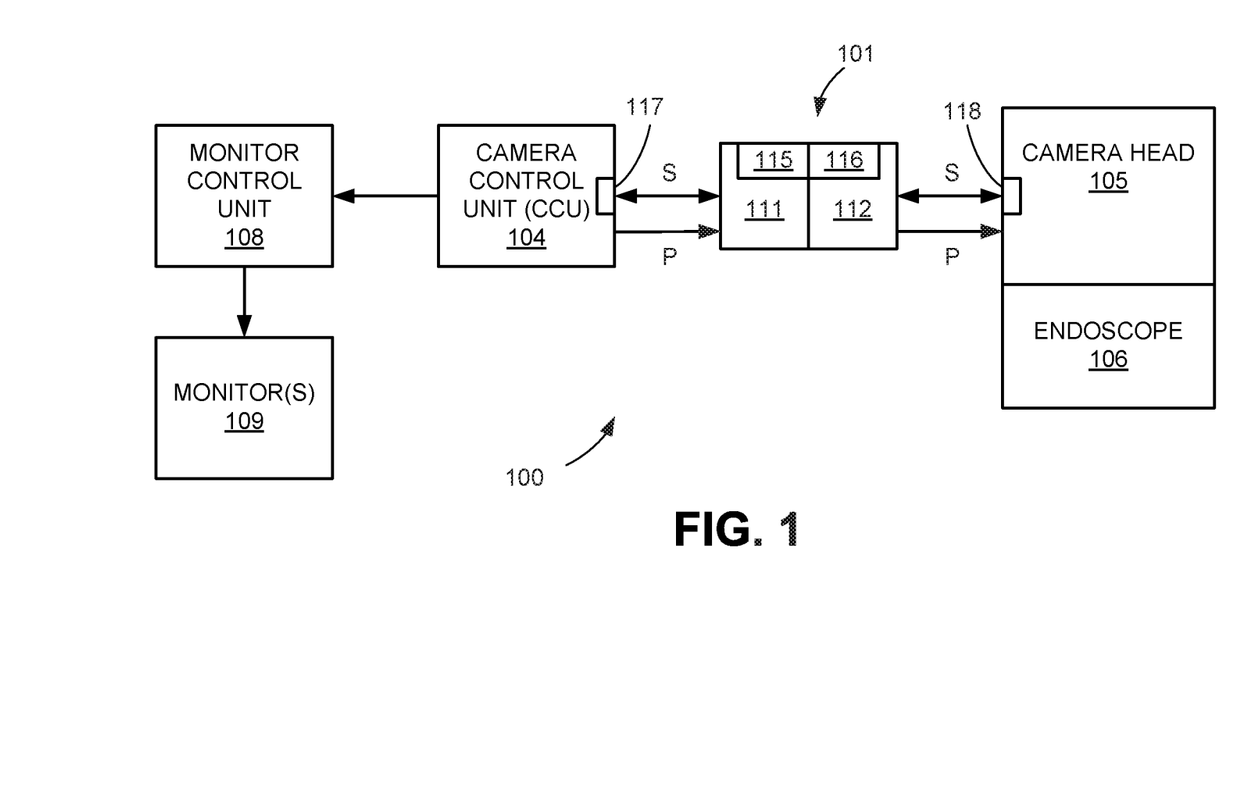
FIG. 1 is a schematic representation of an example system in which an identification apparatus according to one aspect of the invention is implemented.

FIG. 1 shows an endoscopic system 100 employing an interface device 101 in which portions of an identification apparatus according to some aspects of the present invention are implemented. System 100 includes a camera control unit ("CCU") 104, a camera head 105, and an endoscope 106. CCU 104 is connected to send a signal to a monitor control unit 108 which is in turn connected to monitors 109 for displaying images from camera head 105 or endoscope 106.

Interface device 101 is interposed between CCU 104 and camera head 105 and functions as a detachable link for data communication and power transfer between the CCU and camera head. Both the data communication and power transfer functions are preferably provided across interface device 101. This example interface device 101 also maintains an electrical isolation barrier to camera head 105 and endoscope 106 as described in U.S. Pat. No. 10,133,013, issued Nov. 20, 2018, and entitled "Apparatus and Method of Providing an Interface to an Electrically Powered Instrument," the entire content of which is incorporated herein by this reference. Data is communicated in the form of optical data signals S in FIG. 1 bidirectionally, both from camera head 105 and/or endoscope 106 to CCU 104 and also preferably in the opposite direction from the CCU to the camera head and/or endoscope. Electrical power (P in FIG. 1) is transferred unidirectional, in the direction from CCU 104 to camera head 105 and/or endoscope 106.

Interface device 101 includes a first connector 111 and a second connector 112 which may be connected in an operating position to facilitate the desired data communication and power transfer between CCU 104 and the combination of camera head 105 and endoscope 106. In the context of system 100, first connector 111 may be referred to as a control unit-side connector in this embodiment since it is associated with a control unit, namely CCU 104, for the device to be connected (the combination of camera head 105 and endoscope 106). Similarly, second connector 112 may be referred to as a device-side connector in this embodiment since it is associated with the devices or instruments to be connected to a control or other unit.

The operating position between first connector 111 and second connector 112 is schematically indicated in FIG. 1 and will be described in further detail below with reference particularly to FIG. 2. The two connectors 111 and 112 may be readily separated to detach camera head 105 and endoscope 106 from CCU 104 and then reconnected in the operating position as desired. For example, connector 112 may be detached from connector 111 in preparation for sterilizing camera head 105 and/or endoscope 106. Once the sterilization or other process or activity requiring detachment is complete, connectors 111 and 112 may be readily connected back together again in the operating position to again facilitate data communication and power transfer between CCU 104 and camera head 105/endoscope 106.

The position of interface device 101 shown in FIG. 1 between CCU 104 and camera head 105 is intended to indicate that the interface device may be interposed at any position between those two system components. One embodiment that will be described further below in connection with FIGS. 2 and 7 incorporates first connector 111 in a housing for CCU 104. In this embodiment, first connector 111 may be formed as a receptacle in a housing for CCU 104 and adapted to receive second connector 112 in the operating position. Second connector 112 in this embodiment is connected to a suitable cable having optical conduits such as optical fibers for carrying the optical signals and suitable conductors for conducting electrical power to camera head 105. However it should be borne in mind that the invention is not limited to this arrangement in which one of the connectors is incorporated in a control unit such as the CCU 104 or one of the other components in the system.

FIG. 1 shows that interface unit 101 also includes a send/receive unit 115 and a return unit 116 mounted on the first and second connectors, 111 and 112, respectively. These units 115 and 116 each include optical signal path arrangements which are part of an identification apparatus according to various implementations of the present invention. These optical signal path arrangements together with other elements associated with the various optical signal paths included in the arrangements will be discussed below in connection with FIG. 2. As will be described below particularly in connection with the example signals shown in FIG. 3, the optical signal paths and cooperating elements in send/receive unit 115 and return unit 116 cooperate to provide an optical ID encoded with information correlated to one or more characteristics of camera head 105 and/or endoscope 106 (in this representative example).

Before moving on to describe further details of an example identification apparatus, it should be noted that both CCU 104 and camera head 105 in this particular implementation include components for supporting interface 101 and the associated identification apparatus. In particular, CCU 104 includes a transceiver unit 117 which receives optical signals from the direction of camera head 105 and transmits optical signals to the camera head and/or endoscope 106. Similarly camera head 105 includes a transceiver unit 118 for transmitting optical signals to CCU 104 and for receiving incoming optical signals from the CCU. As will be described in detail with respect to FIG. 2 below, transceiver unit 117 also includes components to transmit optical signals to and receive optical signals from send/receive unit 115 for facilitating the identification functionality according to the present invention.

Figure 2:
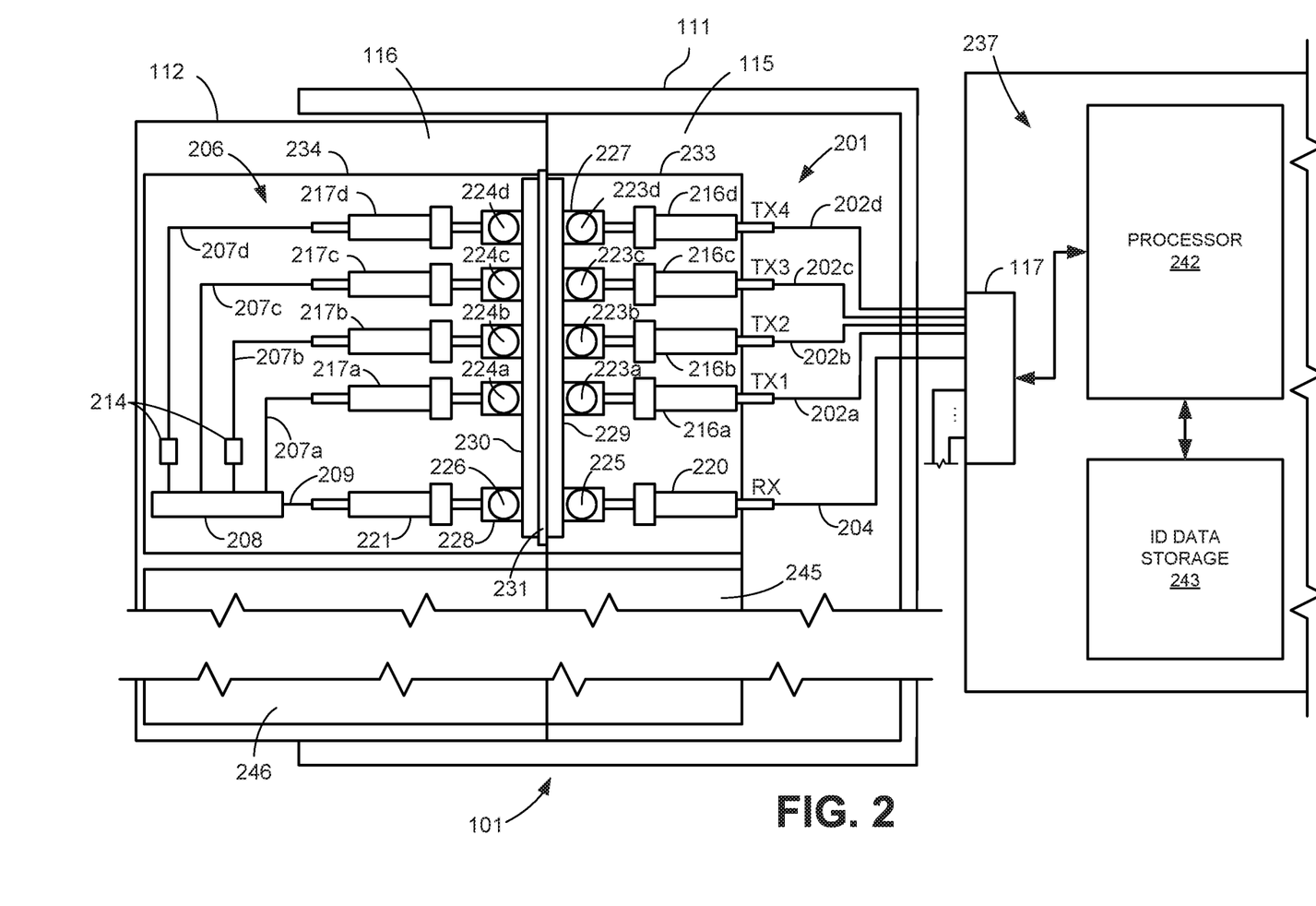
FIG. 2 is a schematic representation of the interface shown in FIG. 1, together with additional components of an example identification apparatus.

FIG. 2 schematically shows further details of first connector 111 and second connector 112. Connector 111 has mounted therein an optical signal transmission path arrangement shown generally at 201. In this illustrated implementation, optical signal transmission path arrangement 201 includes four separate paths defined by separate optical waveguides such as suitable optical fibers 202a, 202b, 202c, and 202d. Connector 111 also includes an optical signal receiving path defined by suitable optical waveguide such as optical fiber 204. These optical signal paths defined in this example by optical fibers 202a-d and 204, together with associated elements described further below which facilitate sending and receiving optical signals to and from connector 112, represent one embodiment of the send/receive unit 115 shown in FIG. 1. Other embodiments having more or less optical fibers are also contemplated. Connector 112 is shown as having an optical signal return path arrangement shown generally at 206. This optical signal return path arrangement 206 extends from an input end, which includes four separate paths in this implementation, to a single output path. The four separate paths at the input end of optical signal return path arrangement 206 may each comprise a suitable optical waveguide such as an optical fiber 207a, 207b, 207c, and 207d. Similarly the single output path may comprise a suitable waveguide such as optical fiber 209. In view of the multiple separate optical paths at the input end of optical signal return path arrangement 206 and the single output path comprising fiber 209, this particular implementation also includes an optical coupler 208 for coupling fibers 207a-d to optical fiber 209. Optical signal attenuators 214 are also shown associated with the optical signal return path. These optical signal attenuators 214 make up an optical signal modification arrangement of the identification apparatus and will be described further below in connection with FIGS. 3 and 4. The combination of optical fibers 207a-d, optical fiber 209, optical coupler 208, and attenuators 214, together with associated elements described below represent the return unit 116 shown in FIG. 1.

In the implementation represented schematically in FIG. 2, each fiber 202a-d terminates in a respective ferrule labeled 216a, 216b, 216c, and 216d in FIG. 2. Each fiber 207a-d also terminates at its input end at a respective ferrule labeled 217a, 217b, 217c, and 217d in FIG. 2. Similarly, FIG. 2 shows that fiber 204 of the optical signal return path terminates at ferrule 220, and fiber 209, which defines the optical signal output path associated with second connector 112, terminates at ferrule 221. The embodiment illustrated in FIG. 2 employs an expanded beam arrangement for transferring optical signals from first connector 111 to second connector 112 and from the second connector 112 to the first connector 111. This expanded beam arrangement includes a respective spherical lens 223a, 223b, 223c, and 223d aligned respectively with each ferrule 216a-d in connector 111 and a respective spherical lens 224a, 224b, 224c, and 224d aligned respectively with each ferrule 217a-d in connector 112. A spherical lens 225 is also aligned with ferrule 220 in connector 111 and a spherical lens 226 aligns with ferrule 221 in connector 112. The spherical lenses of first connector 111 in this embodiment, lenses 223a-d and 225, are each located in a respective lens receiving opening 227 while the spherical lenses 224a-d and 226 of second connector 112 are located in a respective lens receiving opening 228. It should be appreciated that although an expanded beam arrangement is used in transferring the optical signals employed in the apparatus illustrated in FIG. 2, the invention is not limited to use with such arrangements. Rather, the optical signals may be passed between the connectors 111 and 112 in any suitable fashion. Also, where expanded beam arrangements are used, any suitable lens may be used, for example, spliced gradient index lenses, spliced glass rods, or other collimating lenses, to expand and contract the beams, and the invention is certainly not limited to the spherical lenses shown for example in FIG. 2.

Regardless of any arrangement of lenses to facilitate the desired coupling of light signals between connectors 111 and 112, it is desirable to provide a layer of protective material in each connector to protect the respective fibers. Thus the embodiment shown in FIG. 2 includes a protective cover 229 for first connector 111 and a protective cover 230 for second connector 112. These protective covers may comprise sapphire for example, or any other type of material which does not interfere with the transmission of light signals between connectors 111 and 112, and may be separated by an air gap 231 when the connectors 111 and 112 are connected in the operating position.

With second connector 112 connected in the operating position with first connector 111 shown in FIG. 2, the optical signal transmission path arrangement 201 of first connector 111 is operatively aligned with the input end of the optical signal return path arrangement 206 of second connector 112. The operative alignment in this case means that ferrules 216a-d on first connector 111 are each aligned with a corresponding ferrule 217a-d on second connector 112 so that optical signals exiting fibers 202a-d are coupled into the corresponding fibers 207a-d across a respective set of lenses 223a-d and 224a-d, protective covers 229 and 230, and air gap 231. Similarly, ferrule 221 for the fiber 209 defining the output path associated with connector 112 is operatively aligned with ferrule 220 for the fiber 204 defining the optical signal receiving path of connector 111. With this alignment, optical signals from fiber 209 are coupled into fiber 204 across lenses 226 and 225, protective covers 229 and 230, and air gap 231. To help facilitate the operative alignment between the optical paths, the ferrules and spherical lenses are shown mounted in a respective alignment block. In particular ferrules 216*a-d* and 220 along with lenses 223*a-d* and 225 are mounted in an alignment block 233 of first connector 111 while ferrules 217*a-d* and 221 along with lenses 224*a-d* and 226 are mounted in an alignment block 234 of second connector 112.

FIG. 2 also shows transceiver 117 (also referenced above in connection with FIG. 1) and an identification (ID) processing unit 237. Transceiver 117 comprises a suitable device for transmitting the base optical signal and for receiving the optical ID signal both under control of a suitable control device such as ID processing unit 237. Because any suitable optical transceiver may be employed in embodiments of the present invention and because such devices are well known in the art of optical communications, transceiver 117 is shown only schematically in the figures and details of the various components which may be included in such a device are omitted to avoid obscuring the present invention in unnecessary detail. Those familiar with optical signal communications will appreciate that a suitable transceiver may include a respective transmitter such as an electro-optical converter for each fiber 202*a-d* of optical signal transmission path arrangement 201, and a suitable receiver such as an opto-electrical converter for the fiber 204 defining the optical signal receiving path of connector 111. It will also be appreciated that suitable circuitry is included in transceiver 117 for receiving control signals from the associated controller and producing a signal to drive the transmitter(s) and for conditioning the receiver output for use by ID processing unit 237. It should be noted here that the present invention is not limited to any particular wavelength of optical signal for the base optical signal. Rather a base optical signal according to the invention may comprise any light signal that is suitable for propagating through the various optical paths included in the apparatus and amenable for the desired encoding in the second connector and for reception at a suitable receiver.

ID processing unit 237 includes a suitable processor 242 and data storage 243 accessible to the processor. Because connector 111 is integrated with CCU 104 in this particular embodiment of the identification apparatus, transceiver 117, processor 242, and storage 243 may not be components dedicated to the functionality of the identification apparatus. Thus transceiver 117 may include additional transmitters and receivers together with associated circuitry for facilitating the desired communication link between CCU 104 and camera head 104/endoscope 106. These transmitters and receivers are omitted from FIG. 2 similarly to the corresponding elements associated with the identification apparatus. Also processor 242 in this embodiment may provide functionality for the operation of CCU 104 in addition to the functionality of the identification processing unit 237. Similarly data storage 243 may be general data storage (including one or more data storage devices) associated with CCU 104 and may not be dedicated for storing identification information as described further below. Of course, other embodiments of an identification apparatus within the scope of the present invention may include optical transmitters and receivers that are included in a transceiver dedicated exclusively for optical signal transmission and reception for purposes of identification functionalities. The processing unit and associated data storage for providing the desired identification functionality may likewise be devices dedicated to the identification apparatus. In either case, the processor may comprise any suitable digital processor such as a general purpose processor, a field programmable gate array, or an application specific integrated circuit, or combinations of these types of devices.

Because connectors 111 and 112 are connectors for the interface device 101 shown in FIG. 1, the connectors include components for providing the desired communication link between the CCU 104 and camera head 105/endoscope 106 shown in FIG. 1. These components are shown in FIG. 2 as an interface 245 in first connector 111 and interface 246 in second connector 112. These interfaces are shown schematically in FIG. 2 because the specific way in which they provide the desired operative link between the connected device, in this case camera head 105 and endoscope 106, and their control unit, in this case CCU 104, are not relevant to the identification apparatus which is the subject of this disclosure. However, it will be appreciated that interfaces 245 and 246 are located within the respective connector 111 and 112 preferably such that they form the desired operable communication link between CCU 104 and camera head 105 when the various optical paths of the identification apparatus are brought into the operative alignment shown in FIG. 2. This simultaneous operative alignment for elements of the identification apparatus and interfaces 245 and 246 may be facilitated by placing the elements in common alignment blocks for the two connectors 111 and 112. Although interfaces 245 and 246 may take any form suitable for providing the operative link between the devices in question, example interfaces that may be used in particular between an observation unit such as camera head 105/endoscope 106 and a control unit such as CCU 104 are described in detail in the aforementioned U.S. patent application Ser. No. 15/161,007.

Figure 3:
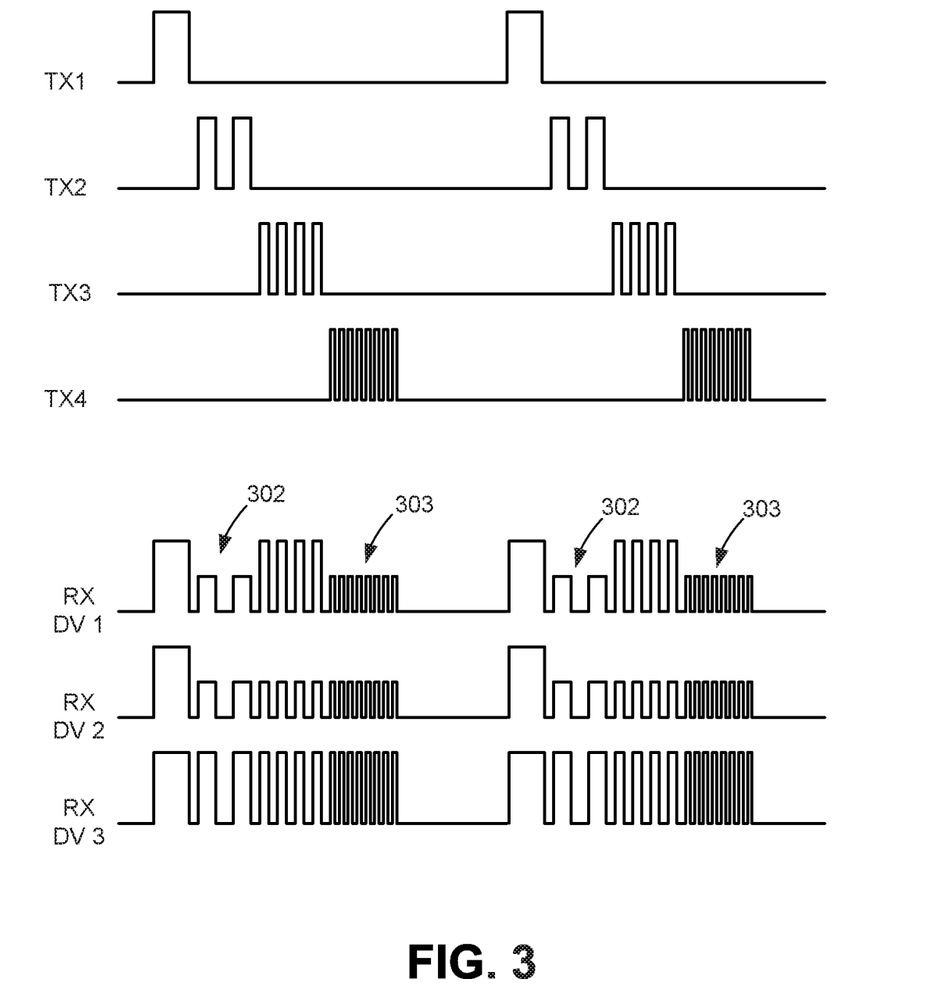
FIG. 3 is a signal diagram showing a representative set of base optical signal components according to one implementation of the present invention, and also showing three examples of optical ID signals which may be produced from the base optical signal components.

The signal diagram of FIG. 3 shows an example of a base optical signal that may be generated according to the present invention. The base optical signal in this example is made up of four different base optical signal components, each expressed in optical power level over time. These include a first base optical signal component shown as signal TX1, a second base optical signal component shown as signal TX2, a third base optical signal component shown as signal TX3, and a fourth base optical signal component shown as signal TX4. These base signal components correspond to the signals transmitted along optical fibers 202*a*, 202*b*, 202*c*, and 202*d*, respectively, in FIG. 2 and are directed across the illustrated expanded beam arrangement to optical fibers 207*a*, 207*b*, 207*c*, and 207*d*, respectively, of second connector 112. In this example, the different base optical signal components each include an optical signal at a different respective modulation frequency and the different signals are offset temporally. Also, FIG. 3 shows each base optical signal component appearing twice over the course of time represented by the horizontal axis of FIG. 3. As will be discussed further below in connection with variations on this example signal arrangement, the optical signals may or may not be all at the same optical wavelength.

FIG. 3 also shows an optical ID signal RX DV1 that is produced by the pattern of modification applied in the optical signal return path arrangement associated with second connector 112 shown in FIG. 2. This signal RX DV1 comprises a signal made up of the various base signal components as modified by signal attenuators 214 and combined via optical coupler 208. As such, signal RX DV1 is a signal present at the output path of second connector 112 defined by fiber 209 and the optical receiving path defined by fiber 204 of first connector 111 in FIG. 2 responsive to the base optical signal comprising the four components TX1, TX2, TX3, and TX4. Thus the base signal components TX1 and TX3 contributing to signal RX DV1 each remain essentially un-attenuated as they travel along their respective fiber 207*a* and 207*c* in FIG. 2 (aside from losses inherent in transmission through the various optical path components).

However, the signal attenuator 214 associated with fiber 207b in FIG. 2 attenuates the signal strength (that is, decreases optical signal power) by a predefined amount as indicated at 302 in FIG. 3. The attenuator 214 associated with fiber 207d similarly attenuates signal TX4 resulting in the attenuated signal indicated at 303 in FIG. 3.

FIG. 3 shows two additional signals as examples of optical ID signals that would be produced by a different arrangement of signal attenuators such as attenuators 214 shown in FIG. 2. The signal pattern shown at RX DV2 in FIG. 3 comprises a signal pattern that would result from placing a signal attenuator 214 in each of fibers 207b, 207c, and 207d of the example device in FIG. 2, while leaving the signal in fiber 207d essentially un-attenuated. The example signal pattern shown at RX DV3 in FIG. 3 comprises a pattern that would result where no attenuator 214 is present in any of the four fibers 207a-d of second connector 112.

The three different signals RX DV1, RX DV2, and RX DV3 show how applying a given pattern of attenuation to the optical signals making up the different components TX1, TX2, TX3, and TX4 of the base optical signal operates to encode information into the base optical signal to create optical ID signals. For example, the un-attenuated signal component may be defined as one binary logical state whereas the attenuated signal may be defined as the opposite logical state. Continuing with this example the un-attenuated signal may be defined as a logical "1" while the attenuated signal may be defined as a logical "0." Applying these example definitions, the signal RX DV1 represents an optical ID signal carrying the binary number "1010," signal RX DV2 represents an optical ID signal encoded as the binary number "1000." And signal RX DV3 represents an optical ID signal encoded as the binary number "1111." The optical ID signal and corresponding binary representation produced by a given signal modification arrangement of a given second connector may be correlated to some characteristic of that connector and particularly a device associated with the second connector. Thus the signal resulting from the signal modification pattern applied in a given second connector may be decoded by an identification processing unit (237 in the example of FIG. 2) to obtain the characteristic associated with the encoded signal. An example of the operations performed by the example identification processing unit 237 in FIG. 2 will be described further below in connection with the flow diagram of FIG. 4.

The present invention encompasses many variations in the base identification signal and the signal modification shown for example in FIG. 3. For example, although FIG. 3 includes four base signal components which may be encoded to represent a four-place binary number, the invention is not limited to any particular number of base signal components provided there remain a sufficient number of components to produce an identifier which may be correlated to the desired device characteristic. Also, the present invention is not limited to any particular encoding arrangement that may be implemented by the signal modification arrangement associated with the second connector. For example, although the encoding shown for example in FIG. 3 indicates that each base signal component may be encoded in a binary fashion, it is possible to encode each component into three or more states in order to increase the amount of data carried by the resulting optical ID signal. In an example of tri-state encoding, different attenuators 214 in FIG. 2 might be selected to reduce the signal power by about half as shown in the attenuation indicated in FIG. 3 to provide one state in addition to an un-attenuated state, and an attenuator blocking the optical signal entirely might be selected to provide a third signal state comprising essentially zero signal power. Of course, the ID processing unit (such as ID processing unit 237 shown in the example of FIG. 2) would then require the capability of distinguishing the three different signal states and convert that information from the ID signal into a usable form such as a binary form.

It should also be appreciated that many different types of base optical signal may be employed to provide a base signal in which information may be encoded via a suitable signal modification arrangement in a connector such as second connector 112. For example, an alternative base optical signal that may be used in an embodiment of the present invention may comprise a signal including different base signal components comprising different optical wavelengths. In this alternative, the signal attenuators (corresponding to example attenuators 214) may comprise wavelength-specific devices operable to attenuate only a specified wavelength or wavelength range included in the base optical signal. In that case, the resulting optical ID signal would include a signal made of up of the various base signal components attenuated or un-attenuated according to the desired encoding pattern provided by the selected wavelength-specific attenuators comprising the signal modification arrangement. Of course, in this wavelength-specific attenuation arrangement, the apparatus would include a suitable transmitter arrangement to generate the different wavelengths and the signal receiving components would be required to distinguish the different signal wavelengths and extract the encoded information on the receiving side. One example implementation employing base optical signal components at different light wavelengths may include a broadband transmitter for producing the base optical signal, and an arrayed waveguide in the optical receiving path of the first connector (corresponding to connector 111 in the above-described example) to separate the different wavelengths for reception at a respective receiver. One advantage of a wavelength-selective modification performed at the second connector (corresponding to connector 112 in the above-described example) is that the optical signal transmission path arrangement and the optical signal return path arrangement may comprise a single waveguide carrying a broadband optical signal or a multiplexed wavelength signal. Signal attenuators in these wavelength-specific modification embodiments may include suitable filters connected in the optical signal return path waveguide to selectively attenuate certain wavelengths as desired to encode the desired information into the optical ID signal.

Although the signal modification performed in the second connector 112 is used to encode information about a characteristic of the connector or a device with which connector is associated, additional information may be encoded into the base optical signal itself. For example, the different modulation frequencies of the signals TX1, TX2, TX3, and TX4 shown in FIG. 3 may be correlated to identify some characteristic of the connector (first connector 111 in the example of FIG. 2) or identify some characteristic of the control unit (such as CCU 104 in the example of FIG. 1) or other device with which the connector is associated. Of course the variation of optical signal modulation frequency shown in FIG. 3 simply represents an example for encoding information about the transmitting unit into the base optical signal, and the invention is not limited to this modulation frequency technique. For example, different combinations of optical wavelengths for the base optical signal components may be correlated to information regarding the transmitting unit.

Figure 4:
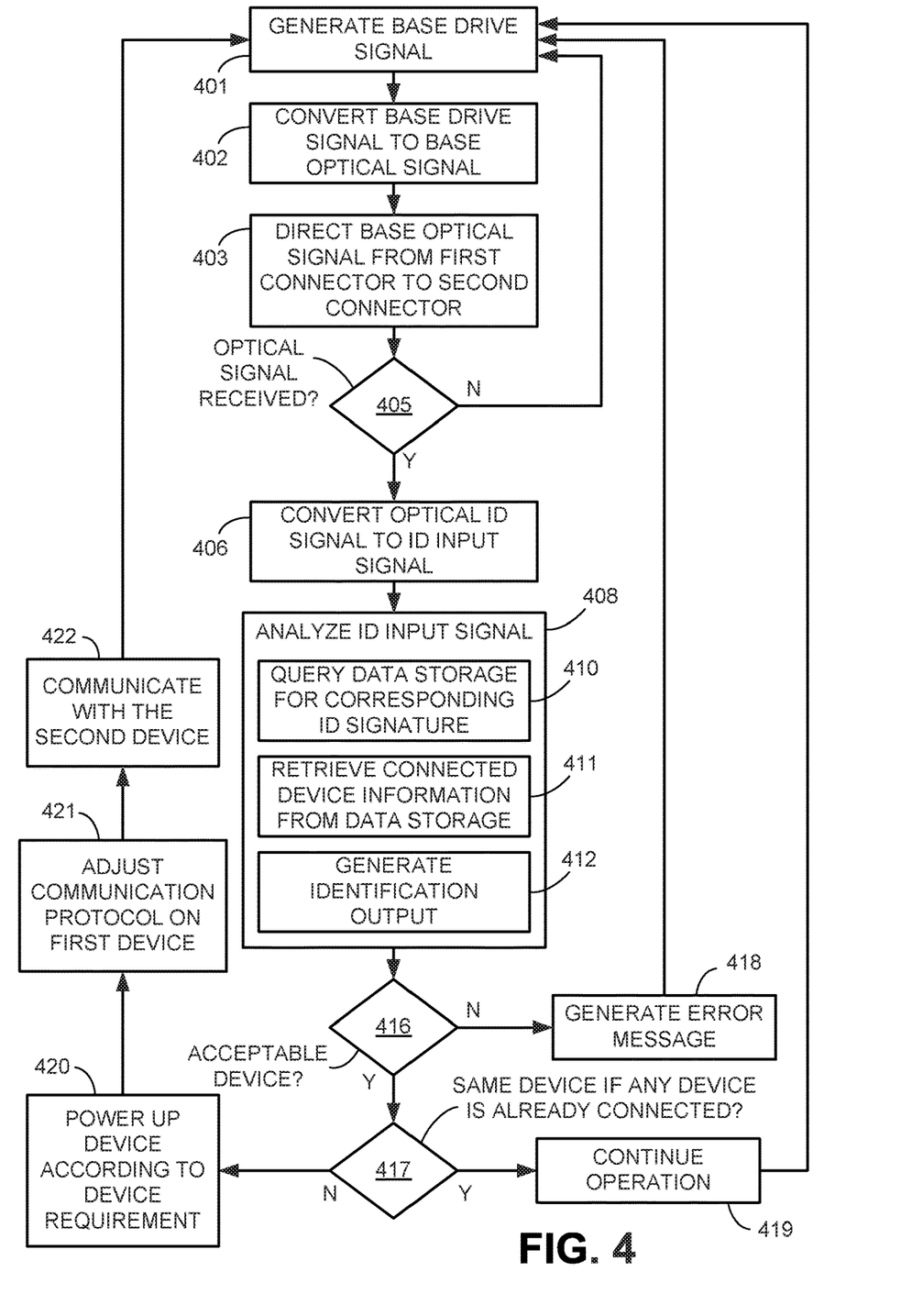
FIG. 4 is a flow diagram showing a process performed on a control unit-side connector of the system shown in FIG. 1.
Figure 5:
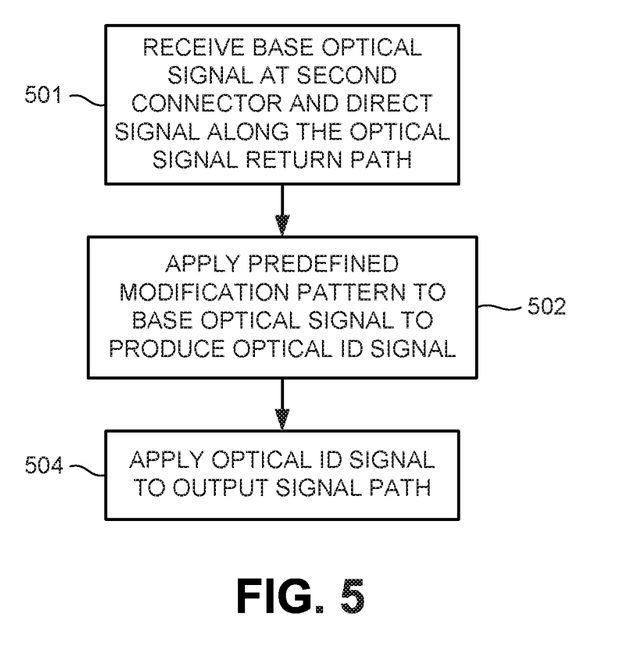
FIG. 5 is a flow diagram showing a process performed at a device-side connector of the system shown in FIG. 1.

The flow diagrams of FIGS. 4 and 5 may now be referenced to describe the operation of the example identification apparatus interface 101 shown in FIG. 2, and methods according to aspects of the present invention. FIG. 4 shows process steps performed on the control unit-side, for example camera control unit 104, of the apparatus 101, while FIG. 5 shows process steps performed on the device-side, for example camera head 105 or endoscope 106, of the apparatus 101. In the following description of FIGS. 4 and 5 it will be appreciated that the references to the apparatus components are references to the components illustrated in FIGS. 1 and 2.

Referring now to FIG. 4, a method of identifying a connected device includes first generating a base drive signal as indicated at process block 401 in FIG. 4. This base drive signal may be generated by circuitry associated with transceiver 117 under control of processor 242 executing suitable program code, and comprises an electrical signal which may be applied to drive transmitters in the transceiver to produce the desired optical signals. The conversion of the electrical drive signal to the base optical signal is shown at process block 402. The base optical signal is then directed from the first connector to the second connector as shown at process block 403. This transfer of the base optical signal from the first to second connector is performed by the optical signal transmission path arrangement shown generally at 201 in FIG. 2, including any associated lenses such as spherical lenses 223a-d.

If no optical signal is received back at first connector 111 in response to the transmission of the base optical signal, it can be assumed that second connector 112 is not present to direct the encoded, optical ID signal to the optical signal receiving path defined in FIG. 2 by fiber 204. In this case the negative outcome at decision box 405 causes the example process to loop back to process block 401 where the base drive signal may be generated again periodically until an optical signal is received. The presence of a signal received from the optical receiving path defined by fiber 204 indicates that second connector 112 is connected in the operating position with first connector 111. In this case the received optical signal directed along the optical receiving path defined by fiber 204 in FIG. 2 is converted to an ID input signal. This conversion indicated at process block 406 in FIG. 4 comprises a conversion of the optical signal to an electrical signal by transceiver 117 in the example of FIG. 2. The ID input signal may then be analyzed as shown at process block 408 in accordance with a suitable process to extract the information encoded into the signal. This analysis is performed in the example system of FIG. 2 by processor 242 in cooperation with data storage 243. In one embodiment, the analysis may include using the ID input signal to query a database stored in data storage 243 for a corresponding ID signature as indicated at process block 410. In the event the ID input signal matches an ID signature in data storage, the process may include retrieving connectable device information that is related to the ID signature in data storage as shown at process block 411. This connectable device information may include one or more characteristics of the connected device such as a device type, or device operating parameters, or a specific serial number for the connected device. Based on this retrieved information the process may include generating an identification output as shown at process block 412.

The process at FIG. 4 includes taking an appropriate action in response to the identification output resulting from the analysis indicated at process block 408. In particular, if the connected device information directly or indirectly indicates that the device is unacceptable to be connected to the particular control unit, CCU 104 in this example, the process may branch from decision box 416 to generating an error message as shown at process block 418. For example, the process at block 418 may include communicating a message to be displayed by the system to a system user to indicate that action is necessary. The identification output generated at process block 412 may also include a suitable communication to CCU 104 to prevent the CCU from placing the connected device in an operational state. Thus the process may then return from block 418 to process block 401 without powering up or otherwise enabling the connected device for use in the given system. However, if the connected device information retrieved at process block 411 indicates that the device is acceptable for use with the given system, identification output generated at 412 may include a communication to CCU 104 indicating that the connected device is appropriate and may be placed in an operational state. In this case the illustrated method proceeds to determine if the identification output generated at 412 indicates that the connected device is the same device identified in the last instance of the process. If the connected device is the same device, the process simply continues operation as indicated at process block 419 and then returns to the start of the process at block 401. However, if the identification output from block 412 indicates that the connected device is a different device than the device connected during the previous instance of the process shown in FIG. 4 or is otherwise a newly connected device, then the process may include enabling the system to power up the connected device as shown at process block 420. This power up according to the device requirement may include providing the correct power supply required by the connected device since the system may support devices having different input power requirements. After the connected device is appropriately powered, the process may include adjusting the communication protocol as necessary to allow communication with the connected device as indicated at process block 421, and then communicating with the connected device as shown at process block 422. The first device referenced in process block 421 may for example comprise a device such as CCU 104 described above, while the second device referenced in process block 422 may comprise the connected device such as camera head 105 described above in connection with FIG. 1. In one embodiment, the process may include periodically proceeding through process steps 401 to 412 to check for a connected device or newly connected device. A loss of return signal in the process shown in FIG. 4 would indicate that the device associated with connector 112 has been disconnected and, in some embodiments, result in an appropriate message at process block 418. The process may then loop back to process block 401 to reinitiate the identification process to identify the next connected device.

FIG. 5 shows the process steps performed at second connector 112 to provide the desired device identification. As shown at process block 501, the process at second connector 112 includes receiving the base optical signal and directing the signal along the optical signal return path arrangement in that connector. The method also includes applying the predefined modification pattern to the base optical signal to produce the optical ID signal as shown at process block 502. In the example of FIG. 2, this application of the predefined modification pattern is performed by the pattern of signal attenuators 214 connected in the fibers 207a-d, and representing the signal modification arrangement. Regardless of the specific manner of signal modification applied by the signal modification arrangement of the second connector, the optical ID signal is then applied to the output signal path as shown at process block 504 so that the signal may be transferred back to the first connector 111 for processing in accordance with the process shown in FIG. 4.

The present invention encompasses numerous variations on the process steps illustrated in FIGS. 4 and 5. For example, although the process shown in FIG. 4 employs the presence of the optical ID signal returned to the control unit-side connector as an indication that the device-side connector is connected in the operating position, other implementations of the invention may additionally or alternatively use other detection techniques. One such technique may employ a suitable sensor device incorporated into the two connectors in addition to or in lieu of the illustrated detection technique. There is also wide variation possible in the steps used to analyze the ID input signal and ultimately produce the identification output as well as wide variation in the identification output itself. For example, the connected device data may be stored in a number of different arrangements to facilitate the retrieval of that data. Where a high level of detail regarding a connected device is desired, the connected device data may include simply a serial number correlated to an ID signature, and this serial number may first be retrieved and then used to obtain further details on the connected device from databases that may be external to the control unit with which the present identification apparatus is employed. In this case, the identification output may be the retrieved serial number which is then used to take further action in response to the connection made between the two connectors incorporating the identification apparatus. More generally the identification output may be any output or series of outputs generated in response to the optical ID signal returned from the second connector.

It should also be noted that although the invention is described particularly in FIGS. 1 and 2 in the context of a device to be identified being connected to a control unit for that device, the invention is not limited to this context. In other implementations, the first connector such as connector 111 in FIGS. 1 and 2 may be a connector associated with some device and the second connector may be a connector associated with some other device or a control unit. In this case, the identification process would be to identify that other device or control unit. Thus the identification would be in essentially the opposite direction from that shown in the example of FIGS. 1 and 2, and the action taken in response to an affirmative outcome at decision box 416 and a negative outcome at decision box 417 in FIG. 4 might be to enable communication or control from the identified connected device. Of course, in this application the device associated with the first connector would include or be associated with a transceiver corresponding to transceiver 117 in FIG. 2 and a processing unit corresponding to 237 in that figure.

Figure 6:
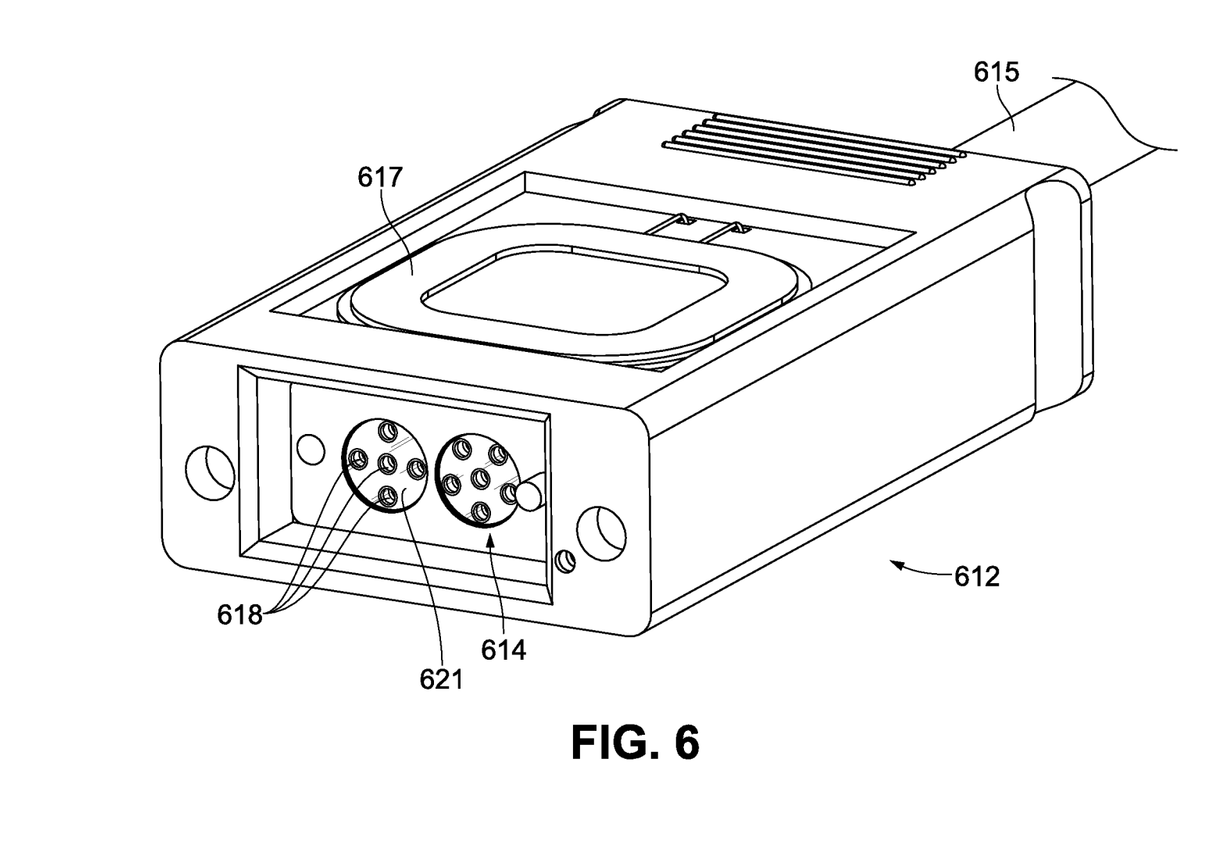
FIG. 6 is a perspective view of a device-side connector according to one aspect of the present invention.
Figure 7:
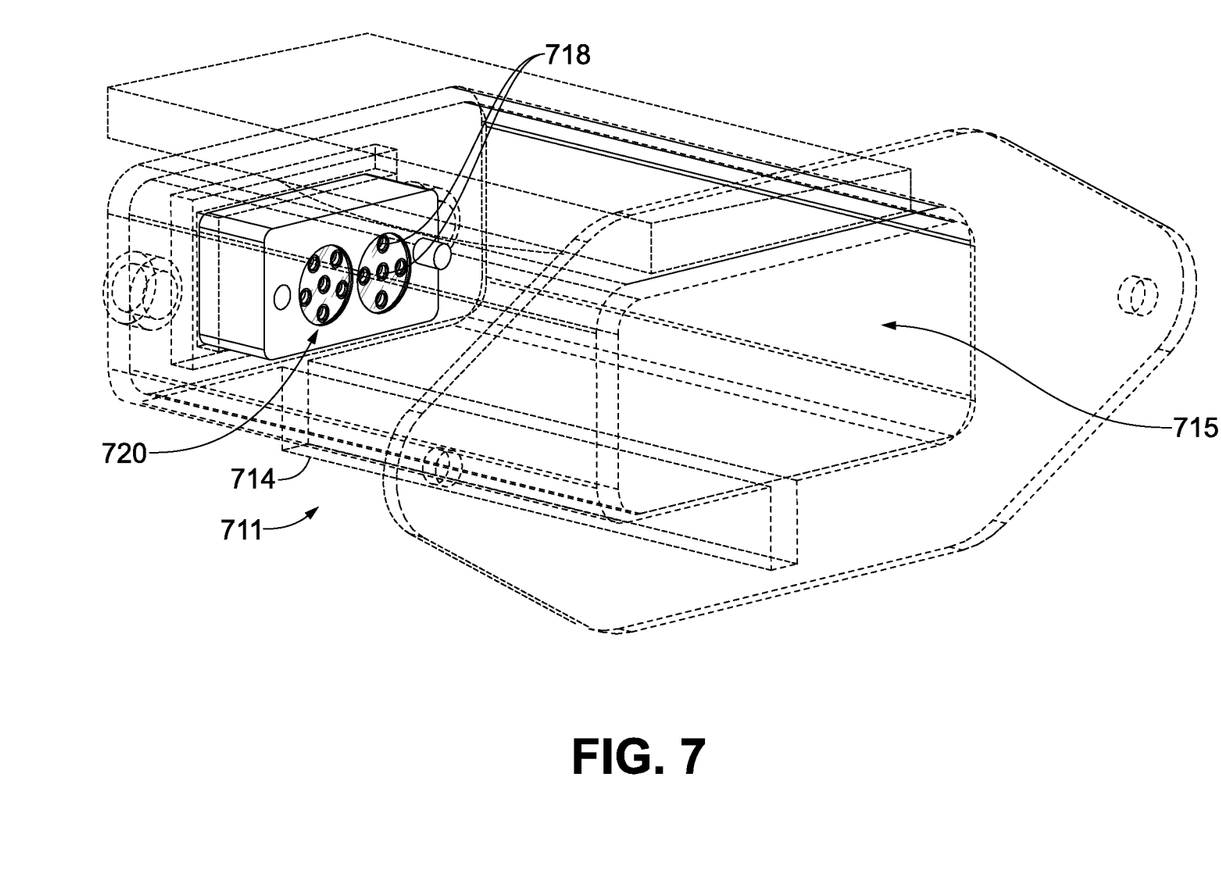
FIG. 7 is a perspective view of a control unit-side connector adapted to cooperate with the device-side connector of FIG. 6 to provide an operative connection between a control unit and a device associated with the device-side connector.

FIGS. 6 and 7 show an example interface corresponding to interface 101 in FIG. 1. In this example, FIG. 6 shows a device-side connector 612 corresponding to second connector 112 in FIGS. 1 and 2, while FIG. 7 shows and example control unit-side connector 711 corresponding to first connector 111 in FIGS. 1 and 2. Connector 612 includes at one end an interface 614 for a device operatively connected to the connector via cable 615. Interface 614 may comprise an optical signal transfer arrangement similar to that shown in incorporated application U.S. patent application Ser. No. 15/161,007. Connector 612 may also include an inductive power coupling coil 617 similar to that shown in this incorporated patent application. However, in addition to interface 614 and power coupling coil 617, connector 612 in FIG. 6 includes an optical path arrangement corresponding to the optical signal return path arrangement 206 shown in FIG. 2. In the perspective of FIG. 6, the only visible portions of the optical signal return path are openings 618 corresponding to lens receiving openings 228 shown in FIG. 2. These openings are visible through protective cover material 621 corresponding to cover material 230 in FIG. 2.

Figure 8:
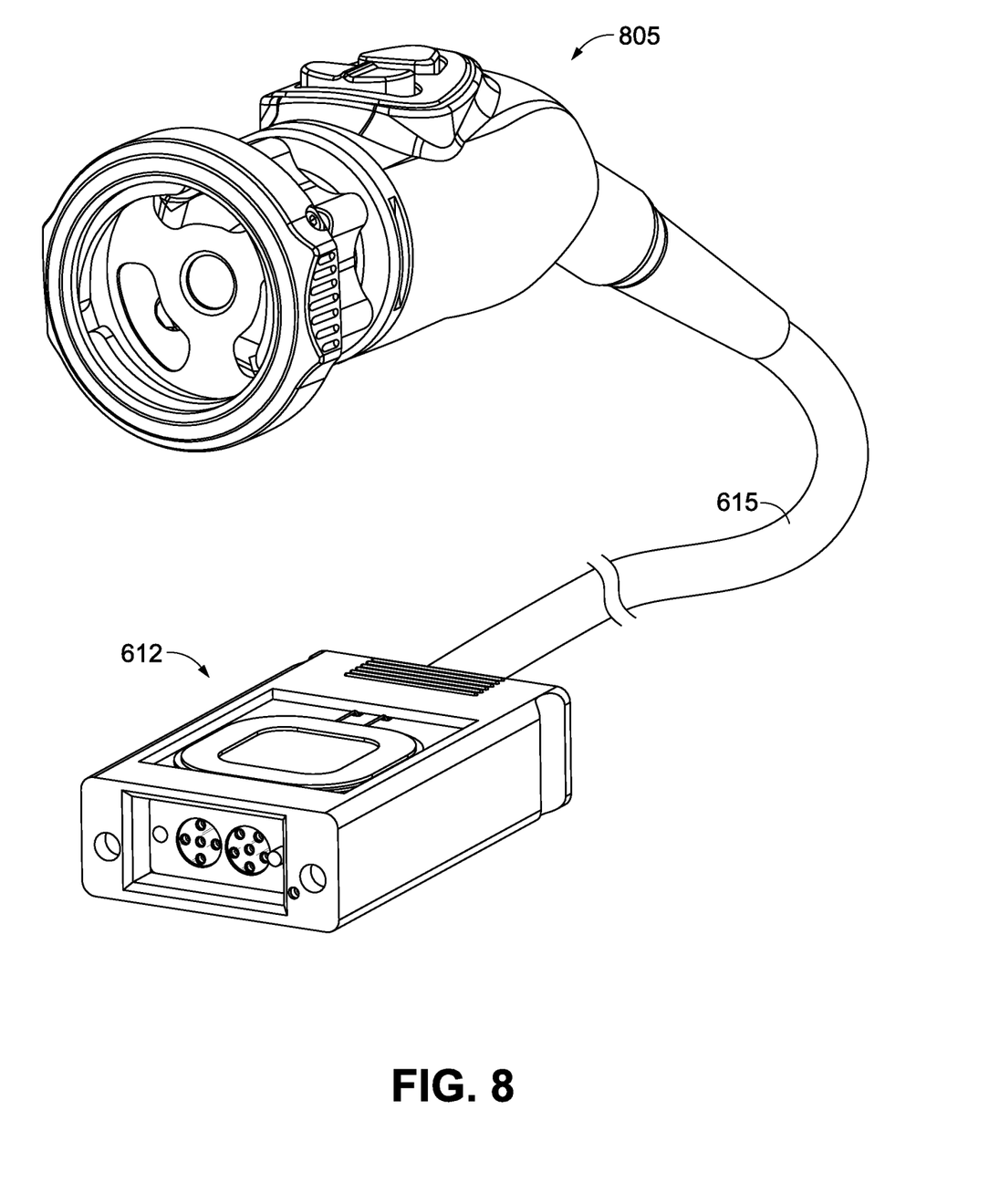
FIG. 8 is a perspective view of a medical device operatively connected to the device-side connector shown in FIG. 6.

Connector 711 shown in FIG. 7 includes a housing 714 which defines a socket 715 in which connector 612 may be inserted to place the two connectors in the operating position. Housing 714 is shown in phantom lines in order to leave certain components of connector 711 visible in the illustrated perspective. In particular, the perspective of FIG. 7 shows openings 718 which correspond to the lens receiving openings 227 associated with the optical signal paths shown for first connector 111 in FIG. 2. The perspective of FIG. 7 also shows an interface 720 adapted to cooperate with interface 614 of connector 612 to provide communications to the device which is associated with connector 612. In this case that device comprises camera head 805 shown in FIG. 8 connected to connector 612 through cable 615.

When connector 711 and its associated housing 714 are operatively connected to a CCU such as CCU 104 in FIG. 1, connector 612 of camera head 805 may be inserted to an operating position in which device interfaces 614 and 720 are operatively aligned as are the openings 618 and 718. According to the process described above in connection with FIG. 4, when connector 612 is so inserted, a base optical signal may be applied from connector 711 to connector 612. This base optical signal is modified to produce an optical ID signal which is then directed to first connector 711. Processing elements of the identification apparatus associated with connector 711 then analyze the optical ID signal to produce an identification output dependent on the result of the analysis and the response options available in the identification system.

As used herein, whether in the above description or the following claims, the terms "comprising," "including," "carrying," "having," "containing," "involving," and the like are to be understood to be open-ended, that is, to mean including but not limited to. Also, it should be understood that the terms "about," "substantially," and like terms used herein when referring to a dimension or characteristic of a component indicate that the described dimension/characteristic is not a strict boundary or parameter and does not exclude variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Any use of ordinal terms such as "first," "second," "third," etc., in the following claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

In the above descriptions and the following claims, terms such as top, bottom, upper, lower, and the like with reference to a given feature are intended only to identify a given feature and distinguish that feature from other features. Unless specifically stated otherwise, such terms are not intended to convey any spatial or temporal relationship for the feature relative to any other feature.

The term "each" may be used in the following claims for convenience in describing characteristics or features of multiple elements, and any such use of the term "each" is in the inclusive sense unless specifically stated otherwise. For example, if a claim defines two or more elements as "each" having a characteristic or feature, the use of the term "each" is not intended to exclude from the claim scope a situation having a third one of the elements which does not have the defined characteristic or feature.

The above described preferred embodiments are intended to illustrate the principles of the invention, but not to limit the scope of the invention. Various other embodiments and modifications to these preferred embodiments may be made by those skilled in the art without departing from the scope of the present invention. For example, in some instances, one or more features disclosed in connection with one embodiment can be used alone or in combination with one or more features of one or more other embodiments. More generally, the various features described herein may be used in any working combination.

The invention claimed is:

1. An identification apparatus comprising:
  (a) a first connector having mounted thereon an optical signal transmission path arrangement and a single optical signal receiving path associated with the optical signal transmission path arrangement;
  (b) a second connector having mounted thereon an optical signal return path arrangement extending from an input end to a single output path associated with the optical signal return path arrangement, the second connector configured to connect to the first connector in an operating position in which the input end of the optical signal return path arrangement is operatively aligned with the optical signal transmission path arrangement and the output path is operatively aligned with the optical signal receiving path;
  (c) an optical signal modification arrangement, comprising one or more optical attenuators, providing a predefined modification to a base optical signal, wherein the base optical signal comprises a plurality of base optical signal components, each expressed in optical power over time, wherein the different base optical signal components each include an optical signal at a different respective modulation frequency, and the different base optical signal components are offset temporally, and applied at the input end of the optical signal return path arrangement, the predefined modification resulting in an optical ID signal applied at the output path of the optical signal return path arrangement;
  (d) an optical transmitter arrangement operable to apply the base optical signal to the optical signal transmission path arrangement;
  (e) an optical receiver operable to receive the optical ID signal from the optical signal receiving path and produce an ID input signal responsive to the received optical ID signal; and
  (f) an identification processing unit connected to receive the ID input signal, the identification processing unit comprising data storage coupled to at least one of a hardware general purpose processor, a field programmable gate array, or an application specific integrated circuit, and being operable to produce an identification output responsive to the ID input signal.

2. The identification apparatus of claim 1 wherein:
  (a) the optical signal transmission path arrangement comprises two or more transmission optical waveguides;
  (b) the optical signal receiving path comprises a receiving optical waveguide;
  (c) the input end of the optical signal return path arrangement comprises a respective return optical waveguide for each transmission optical waveguide, each respective return optical waveguide being located in the second connector so as to operatively align with the respective transmission optical waveguide when the second connector is connected with the first connector in the operating position;
  (d) the output path comprises an output optical waveguide located in the second connector so as to operatively align with the receiving optical waveguide when the second connector is connected with the first connector in the operating position; and
  (e) an optical coupler positioned in the optical signal return path arrangement so as to optically couple each return optical waveguide to the output optical waveguide.

3. The identification apparatus of claim 2 wherein the optical signal modification arrangement comprises two or more non-variable optical signal attenuator, each respective optical signal attenuator operatively connected in a respective one of the return optical waveguides.

4. The identification apparatus of claim 2 wherein each of the two or more transmission optical waveguides includes a respective transmission end portion extending substantially parallel to a receiving end portion of the receiving optical waveguide.

5. The identification apparatus of claim 1 wherein:
  (a) the optical signal transmission path arrangement and the optical signal receiving path are mounted within a transmit and receive alignment block which is mounted in the first connector; and
  (b) the optical signal return path arrangement is mounted in a return alignment block which is mounted in the second connector.

6. The identification apparatus of claim 1 wherein:
  (b) the first connector includes a medical instrument control unit interface; and
  (b) the second connector includes a medical instrument interface configured to operatively connect to the medical instrument control unit interface when the second connector is connected to the first connector in the operating position.

7. The identification apparatus of claim 1 wherein the identification processing unit comprises:
  (a) data storage storing a number of ID signatures, each respective ID signature related in the data storage to respective connectable device information; and
  (b) a processor operable to, in response to the received ID input signal, (i) locate in the data storage one of the ID signatures corresponding to the ID input signal and retrieve the respective connectable device information related to the located ID signature, and (ii) generate the identification output based on the respective device information related to the located ID signature.

8. A method comprising:
  (a) transmitting a base optical expressed in optical power over time, from a first connector to a second connector, the base optical signal including two or more base optical signal components each expressed in optical power over time, wherein the different base optical signal components each include an optical signal at a different respective modulation frequency, and the base optical signal components are offset temporally;

(b) directing the base optical signal along an optical signal return path arrangement associated with the second connector;
(c) applying a predefined modification pattern to the two or more base optical signal components as the base optical signal is directed through the optical signal return path arrangement, the predefined modification pattern resulting in an optical ID signal applied at an output waveguide of the optical signal return path arrangement;
(d) directing the optical ID signal from the output waveguide to a receiving optical waveguide of the first connector; and
(e) receiving the optical ID signal at the first connector and producing an identification output in response to the received optical ID signal.

9. The method of claim 8 wherein the predefined modification pattern comprises a pattern of signal attenuation among the two or more base optical signal components.

10. The method of claim 8 wherein:
(a) transmitting the base optical signal includes directing each respective base optical signal component over a different respective transmission optical waveguide associated with the first connector; and
(b) directing the base optical signal along the optical return path arrangement includes directing each base optical signal component along a different respective return optical waveguide associated with the second connector.

11. The method of claim 10 wherein the predefined modification pattern comprises a pattern of signal attenuation among the two or more base optical signal components.

12. The method of claim 8 further including:
(a) producing an ID input signal in response to the optical ID signal;
(b) locating in data storage an ID signature corresponding to the ID input signal;
(c) retrieving connectable device information related in the data storage to the located ID signature; and
(d) generating an identification output based on the retrieved device information.

13. An apparatus comprising:
(a) an instrument;
(b) an instrument connector operatively connected to the instrument, the instrument connector configured to connect in an operating position with a control unit connector associated with a control unit for the instrument;
(c) an optical signal return path arrangement mounted in the instrument connector, the optical signal return path arrangement extending from an input end to an output optical waveguide; and
(d) an optical signal modification arrangement associated with the optical signal return path arrangement and operable to provide a predefined modification to a base optical signal, wherein the base optical signal comprises a plurality of base optical signal components, each expressed in optical power over time, wherein the different base optical signal components each include an optical signal at a different respective modulation frequency, and the different base optical signal components are offset temporally, and applied at the input end of the optical signal return path arrangement, the predefined modification resulting in an optical ID signal applied at the output optical waveguide.

14. The apparatus of claim 13 wherein the input end of the optical signal return path arrangement includes two or more return optical waveguides and an optical coupler coupling each return optical waveguide to the output optical waveguide.

15. The apparatus of claim 14 wherein the optical signal modification arrangement comprises at least one non-variable optical signal attenuator, each respective optical attenuator operatively connected in a respective one of the return optical waveguides.

16. The apparatus of claim 14 wherein each of the two or more return optical waveguides includes a respective end portion extending substantially parallel to an output end portion of the output optical waveguide.

17. The apparatus of claim 13 wherein the optical signal return path arrangement is mounted in a return alignment block in the instrument connector.

18. The apparatus of claim 13 wherein the instrument connector includes an instrument interface configured to operatively connect to a control unit interface of the control unit connector when the instrument connector is connected to the control unit connector in the operating position.

* * * * *